United States Patent [19]

Yen

[11] Patent Number: 5,308,620

[45] Date of Patent: May 3, 1994

[54] PROTEIN NANOMATRIXES AND METHOD OF PRODUCTION

[75] Inventor: Richard C. K. Yen, Glendora, Calif.

[73] Assignee: Hemoshpere, Inc.

[21] Appl. No.: 959,560

[22] Filed: Oct. 13, 1992

Related U.S. Application Data

[63] Continuation-in-part of Ser. No. 641,720, Jan. 15, 1991, abandoned.

[51] Int. Cl.$^5$ ................................. A61K 9/14
[52] U.S. Cl. ................................. 424/484; 424/486; 424/489; 424/499; 252/315.1
[58] Field of Search ............... 424/484, 489, 491, 486, 424/499; 530/333, 412, 422, 424, 427; 252/308, 315.1; 514/2, 21

[56] References Cited

U.S. PATENT DOCUMENTS 4,447,355 5/1984 Sakamoto et al. ............... 260/112 B
5,049,322 9/1991 De Vissaguet et al. .............. 264/4.1

OTHER PUBLICATIONS

Remington's Pharma. Sci. 1985, p. 271.

Lehninger Biochemistry 1972, p. 134.

*Primary Examiner*—G. S. Kishore
*Attorney, Agent, or Firm*—Thomas I. Rozsa; Tony D. Chen

[57] ABSTRACT

The present invention is a novel method of producing a unique device of stable porous and membraneless nanomatrixes for carrying medication for in vivo administration. The present invention method produces the device of stable nanomatrixes by mixing a first type of protein which is hemoglobin, a second type of protein which is albumin, and a solution containing an organic solvent which is an alcohol, where the weight ratio of the first and second type of proteins is within the range of approximately 92±5 to 8±5. This results in a turbid suspension of monodispersed nanomatrixes which are typically larger than 1 micron but less than 4 microns in diameter and stable against aggregation and re-solubilization in hypotonic saline for at least 24 hours. An additional solution containing a biologically active substance may be added before or after the solution containing an organic solvent, such that the biologically active substance is entrapped within or bound on the surfaces of the nanomatrixes.

5 Claims, No Drawings

PROTEIN NANOMATRIXES AND METHOD OF PRODUCTION

This Patent Application is a Continuation-In-Part of patent application Ser. No. 07/641,720 filed on Jan. 15, 1991, now abandoned.

BACKGROUND OF THE INVENTION

1. Field of The Invention

The present invention relates to the field of in vivo medication carriers for intravenous drug administration and methods of production. More particularly the present invention relates to the field of carrying of drugs in particulate vehicles which are porous and membraneless for intravenous drug administration and methods of production.

2. Description of The Prior Art

Conventional methods of drug administration include oral, intramuscular, subcutaneous, intraperitoneal, and intravenous injections. Of these methods, the intravenous approach allows the most direct and fastest equilibration with the blood stream which carries the medication to the rest of the body. However, peak serum levels are achieved within a short time of intravascular injection of any drugs. Toxic effects can result from such high serum levels, especially if the drug is given as a bolus injection. To avoid such high concentrations, drugs can be given slowly as a continuous drip. However, the latter method would require prolonged nursing care and possibly even hospitalization with its associated cost. Administration of drugs carried within stable carriers would allow bolus intravenous injections but gradual release of the drugs inside the intravascular compartment.

Another consideration of drug release is the uptake of the carrier by the reticulo-endothelial system (RES), allowing greater delivery of drugs to the liver and spleen. Alternatively, if the carriers are small enough so that the phagocytic cells (e.g. macrophage) do not preferentially ingest them, the carriers would escape the RES long enough to perform other tasks. One such interesting and medically useful task would be targeting of drugs to a specific population of cells. The targeting of specific cell types would be carried out by carriers which had antibodies or other ligands on the surface of the carriers directed against antigenic sites or specific receptors of these cells. Higher concentrations of drugs near the surface of the targeted cells and lower systemic side-effects would be desirable benefits from this approach.

Entrapment of biological agents are useful in other medical applications. For example, tiny air bubbles can create a strong contrast of the blood vessels (and the organs within which the blood vessels traverse) against the background during ultrasonography. However, the tiny air bubbles, if injected via a peripheral vein, must travel through the right heart, the pulmonary vasculature and then the left heart before they can reach to the other internal organs. Tiny air bubbles are inherently unstable and so they will not be able to stay in the required physical condition for effective ultrasonographic contrast by the time the intended organs are reached. Entrapment of the small air bubbles in small carriers will allow the air bubbles to serve their intended function even after long distances of travel within the intravascular compartment.

Similar advantages can be conferred to contrast material for CAT scans and nuclear magnetic resonance (NMR) scans. By entrapment of the contrast material during injection, the injection site will not have an abnormally high concentration of the contrast material leading to false interpretation of the results. However, the reticula-endothelial system (RES), such as the liver and the spleen, with the many phagocytic cells there, tend to phagocytize particulate matter. Uptake of contrast material such as paramagnetic metal ion chelate (e.g. $Fe_3O_4$ and Gadolinium-DTPA chelate) by the RES would lead to digestion of carrier whereby the contrast agent is released for enhancement of the organs during magnetic resonance imaging.

Oxygen is another vital biological molecule that can be carried within the carrier if the carrier contains hemoglobin. It is now recognized that hemoglobin molecules, when given in large amounts, are toxic to the human body. Entrapment of hemoglobin within the carrier may reduce its toxicity to vital organs while allowing oxygen to be delivered.

From the above discussion it is clear that stable porous and membraneless carriers which allow rapid diffusion of biological molecules between their interiors and their environments offer many advantages. The two major approaches of microsphere synthesis in the prior art are liposomes and microspheres.

In liposomes, a shell is formed by a lipid layer or multiple lipid layers surrounding a central hydrophilic solution containing the medication. The lipid layers are inherently unstable and much research went into stabilizing them during the manufacturing process. In addition, the lipid layer(s) may serve as a barrier to diffusion of certain molecules. It is difficult for hydrophilic substrate to diffuse through the hydrophobic layers into the interior of the liposomes, or conversely, for the drugs to get out without physical destruction of the lipid layer(s).

Microspheres, in contrast to liposomes, do not have a surface membrane or a special outer layer to maintain its intactness. Most microspheres are more or less homogenous in structure. To maintain the stability of the microspheres, the manufacturing process in prior arts always includes a cross-linking process to stabilize the microspheric mass. However, the use of cross-linking agent in the manufacturing process will alter the chemical nature of the natural biological molecule, which may render the resultant product antigenic to the injected host. Anaphylactic reaction to such newly created antigenicity is unpredictable and dangerous.

The following prior art reference are found to be relevant to the field of the present invention.

U.S. Pat. No. 4,107,288 issued to Oppenheim et al. on Aug. 15, 1978 for "Injectable Compositions, Nanoparticles Useful Therein, And Process of Manufacturing Same" (hereafter "Oppenheim") discloses a process of making microspheres of cross-linked macromolecules by using cross-linking agents such as an aldehyde hardening agent (e.g. glutaraldehyde). In addition to the hardship in controlling the sizes of the microspheres formed, the Oppenheim process also produces many aggregations which are very undesirable for the purpose of an in vivo medication carrier.

U.S. Pat. No. 4,269,821 issued to Krauter et al. on May 26, 1981 for "Biological Material" (hereafter "Krauter") discloses processes for preparation of submicroscopic particles of physiologically acceptable polymer associated with a biologically active material by using a cross-linking agent such as a polymerisable material soluble in a liquid medium (e.g. methyl methacrylate).

U.S. Pat. No. 3,663,685 issued to Evans et al. on May 16, 1972 for "Biodegradable Radioactive Particles" (hereafter "Evans") discloses a method of preparing biodegradable radioactive particles by using heated wateroil solutions.

The article entitled "Magnetically Responsive Microspheres And Other Carriers For The Biophysical Targeting Of Antitumor Agents" written by Widder et al. and published in 1979 at *ADVANCES IN PHARMACOLOGY AND CHEMOTHERAPY*, Vol. 16, pp. 213-271 (hereafter "Widder") discloses emulsion polymerization methods of preparation of albumin microspheres (pp. 233-235) and preparation of magnetically responsive albumin microsphere (pp. 241-250). The methods essentially involve the processes of emulsification and heat denaturation of a water-oil solution to produce and stabilize microspheres. Widder has also mentioned that for heat sensitive drugs the microspheres are stabilized by chemical cross-linking.

As discussed above, some typical prior art processes, such as those used by Oppenheim et al. and Krauter et al., require the irradiation or heat or the presence and chemical reaction of a cross-linking agent to polymerize the "monomers" (which are the individual protein molecules such as human serum albumin or gelatin molecules) so that the resultant "polymers" will increase in molecular weight. When the mass has reached to the point that the solution cannot hold it in its soluble form, the mass will precipitate as a solid more-or-less spherical form which is the microsphere. The covalent bonding of the "monomers" into a "polymer" by the cross-linking agent provides the stability of the microsphere.

Other prior art methods, such as used by Widder et al. and Evans et al., use heat to cross-link and to stabilize the protein mass. Essentially, the emulsion consisting of microscopic protein droplets are heated in oil so that the proteins are denatured as a microscopic particle and stayed that way upon cooling and removal of the oily compounds. These protein molecules have been irreversibly denatured and rendered "foreign" to the host body.

U.S. Pat. No. 5,049,322 issued to Devissaguet et al. on Sep. 17, 1991 (hereafter "Devissaguet") discloses a method of producing a colloidal system containing 150-450 nm particles by dissolving a protein ingredient in a solvent and adding ethanol or mixture of ethanol containing surfactant. Devissaguet does not disclose adding a second protein ingredient. Devissaguet discloses a process of producing colloidal spheres which have a distinct "Wall" (column 2, line 25) or "layer" (column 8, line 33) of substance A which is different from the "core" of substance B (column 8, line 18), where the substance B may be a biologically active substance.

Devissaguet's method requires that substance A (the wall material) and substance B (the core material that is desired to be encapsulated) to be both present in the first liquid phase, which is then added to a second liquid phase that is a non-solvent for both substances A and B. Devissaguet's product consists of a "wall" formed by substance A, enclosing a "core" formed by substance B. It is clear the substance A is located physically in a different region than substance B, where substance A is on the outside and substance B is on the inside.

Albert L. Lehninger, *Biochemistry: The Molecular Basis of Cell Structure and Function* (1972) (hereafter "Lehninger") discloses that ethanol as a solvent can decrease the ionization of proteins and therefore promotes their coalescence and produces "colloidal suspensions". Lehninger does not disclose a special method of preparing colloidal suspensions, but rather generally a method of promoting protein coalescence by using ethanol, "[s]ince a decrease in dielectric constant increases the attractive force between two opposite charges, ethanol decreases the ionization of proteins and thus promotes their coalescence" (page 134, lines 21 through 25, citations omitted). Lehninger has defined the process of "coalescence" as a process leading to "insoluble aggregates" (page 133, lines 31 through 35). The desirable process, however, should not result in aggregates.

"Remington's Pharmaceutical Sciences", 7th ed. (1985) (hereafter "Remington") discloses some general knowledge of "colloidal dispersions". Remington teaches that adding surfactant "stabilizes the dispersion against coagulation" (page 286, column 2, lines 59 and 60), where the surfactant "arrange themselves at the interface between water and an organic solid or liquid of low polarity in such a way that the hydrocarbon chain is in contact with the surface of the solid particle or sticks inside the oil droplet while the polar bead group is oriented towards the water phase" (page 286, column 2, lines 30 through 35). Remington does not specially disclose the use of any particular protein molecules such as globin as the primary protein.

It is highly desirable to have an efficient synthetic method which does not involve the using of cross-linking agents nor heating, to thereby produce an effective carrier product which has desirable properties, including: (a) well controlled sizes, whether the goal is to produce carriers as small as 0.1 micron or as large as 7 micron in diameter; (b) stability against dilution (or removal of unreacted material by repeated washing) in a medium different from the one from which the carrier is synthesized; (c) stability against aggregation in various in vitro buffers with high or low osmolarity and in vivo.

The present invention is called "nanomatrixes" because some of them can be less than 50 nanomatrixes in diameter, although some can be as large as 4 to 5 microns. They are called "matrixes" because they do not have an enclosing membrane, much as a cotton ball having no need of a wrapper to maintain its shape. Their surfaces and interiors are continuously porous, which allows ready diffusion of molecules inward or outward.

SUMMARY OF THE PRESENT INVENTION

The present invention is a method of producing protein nanomatrixes and the products produced therefrom.

It is known that microscopic particles such as protein microspheres are used as in vivo encapsules carrying medication. Prior art methods of producing protein microspheres typically involve adding cross-linking agents or heating to cross-link and stabilize the microspheres. It is desirable that stable drug carriers be synthesized without gross denaturation or interaction with cross-linking agents.

It is also known that it is desirable to have microscopic particles being uniform in size and small enough so that they do not obstruct the human blood capillaries which are typically about 7 microns in diameter. The protein microspheres produced by prior art methods often contain many aggregates of much larger size.

It has been discovered, according to the present invention, that microscopic particles can be formed by using a novel and unique method of simply mixing suitable stable ingredient solutions under ambient conditions, without heating or adding cross-linking agents. These particles are stable and do not redissolve easily in buffers different from the synthesis buffer in vitro and in vivo.

It has also been discovered, according to the present invention, that the microscopic particles produced by the novel and unique method of the present invention are larger than 1 micron in diameter, although particles with less than 1 micron in diameter can be obtained by slight modification of synthesis conditions. The particles are called "nano"-matrixes to more conveniently describe the size of the smaller particles, which can be less than 0.05 micron (which is below the resolution of the light microscope). Particles larger than 1 micron will settle to the bottom of the container while smaller particles can remain suspended by Brownian movements for months.

It has also been discovered, according to the present invention, that these protein carriers do not have an enclosing membrane which distinguishes the surface in contact with the exterior environment versus the interior of the carrier. Rather, the protein material forms a continuous mass linking the surface directly with the interior; much like a cotton ball, the exposed surface of which is a continuation of the interior material without the existence of an enclosing membrane.

It has also been discovered, according to the present invention, that when properly produced by the novel and unique method of the present invention, the nanomatrixes are completely monodispersed with no aggregates and very stable in the synthetic media for a substantial length of time.

It has also been discovered, according to the present invention, that biologically active molecules, e.g., enzymes, can be entrapped uniformly within these microscopic particles if these molecules are added to the protein solutions before addition of an alcohol solution.

It has also been discovered, according to the present invention, that biologically active molecules, e.g., ligands, antibodies (e.g. hemagglutinin molecules) can be attached non-covalently to the surface of the carriers and retain their specificity against the proper receptors, if the biologically active molecules are added soon after the addition of an alcohol solution.

It has also been discovered, according to the present invention, that the yield of protein carriers from initial protein solution will be increased when the amount of desolubilizing agent to be added to the protein solution is increased.

However, excessive amounts of desolubilizing agent will lead to uncontrollable aggregation of protein molecules.

It has further been discovered, according to the present invention, that pure hemoglobin (Hb) nanomatrixes could be synthesized in a normal saline buffer but they are unstable and tend to aggregate together if not further stabilized by a second protein, e.g. human serum albumin (HSA), soon after the formation of pure Hb nanomatrixes.

It has been further discovered, according to the present invention, that pure Hb particles synthesized under maximal yield conditions can be stabilized against aggregation after their formation, by addition of a second protein (e.g, HSA or immunoglobulin) to approximately 2.5 mg/m]concentration.

It has been further discovered, according to the present invention, that when the concentration of HSA is less than 2.5 mg/Ml in the presence of approximately 5 mg/ml Hb before the addition of an alcohol solution, the nanomatrixes produced under condition to obtain maximal yield of nanomatrixes, these nanomatrixes can still be stabilized against aggregation if an additional amount of HSA is added within 10 minutes after appearance of turbidity, to bring the total concentration of HSA to at least 2.5 mg/ml. These particles are typically larger than 1 micron.

It has been further discovered, according to the present invention, that the presence of human serum albumin (HSA) of more than 4% (weight of HSA per total weight of protein) in the initial solution will provide stability to the primarily Hb nanomatrixes (about 96% by weight of total protein mass) when the amount of alcohol used is less than that required to produce maximal amount of particles. A higher HSA to hemoglobin ratio also resulted to form progressively smaller nanomatrixes.

It has further been discovered, according to the present invention, that pure Hb nanomatrixes could also be synthesized in water but they are unstable and tend to aggregate together. Presence of at least one of stabilizer such as sodium lauryl sulphate (STS) or Gelatin will provide stability to the primarily Hb nanomatrixes.

It has further been discovered, according to the present invention, that a higher gelatin to hemoglobin ratio resulted in smaller nanomatrixes. No significant difference in size was observed by using a higher HSA to hemoglobin ratio on nanomatrixes synthesized in butanoll but a difference in size was observed by using a higher HSA to hemoglobin ratio on nanomatrixes synthesized in propanol.

It has further been discovered, according to the present invention, that higher concentrations of hemoglobin solution resulted in larger nanomatrixes, and at least 4.76 percent by weight of gelatin is needed for preventing aggregates occurring in synthesis of Hb nanomatrixes.

It has further been discovered, according to the present invention, that the absence of a stabilizer such as hemoglobin from HSA solution resulted in unstabilized synthesis or useless aggregates. However, inclusion of as little as 1.48% of hemoglobin will greatly increase the stability of the HSA nanomatrixes.

It has further been discovered, according to the present invention, that a substantially high concentration of surfactant resulted in larger HSA nanomatrix size; excessive surfactant even resulted aggregates. When a critical amount of co-surfactant was exceeded by a small amount, the result was aggregated spheres instead of monodispersed nanomatrixes. The highest final concentration of nondialyzed HSA (before addition of co-surfactant) that can produce monodispersed nanomatrixes is 148 mg/ml. With dialyzed HSA the final concentration that can be used to produce monodispersed nanomatrixes may be higher. Also, methanol tends to produce smaller spheres than ethanol. It may be possible that a low STS concentration such as 1.4 mg/ml in conjunction with methanol would produce useful nanomatrixes with final concentrations of dialyzed HSA even higher than 148 mg/ml. Different co-surfactants have different effects on the sizes of Hb and HSA nanomatrixes.

It has further been discovered, according to the present invention, that drugs or biologically effective molecules trapped by Hb and HSA nanomatrixes are stable. Also, the biological agents prebonded to hemoglobin molecules can be incorporated into Hb nanomatrixes.

It is therefore an object of the present invention to provide a novel and unique method of producing protein nanomatrixes without cross-linking process or agent and yet the nanomatrixes are stable and do not readily redissolve in a different in vitro buffer or in vivo.

It is also an object of the present invention to provide protein nanomatrixes which are uniform in size and are porous, which allows them to serve as effective medication carriers.

It is a further object of the present invention to provide almost pure hemoglobin (Hb) nanomatrixes synthesized in a normal saline buffer stabilized by human serum albumin (HSA) which have sizes larger that 1 micron to facilitate sedimentation by gravity without aggregation..

It is a further object of the present invention to provide nanomatrixes which can entrap biologically active molecules, e.g., enzymes, toxins, nutrients, uniformly in the matrix of the particles.

It is a further object of the present invention to provide nanomatrixes which can bind non-covalently biologically active molecules (e.g., ligands, antibodies, receptor recognition molecules) on the surface of the particles.

It is a further object of the present invention to provide almost pure Hb nanomatrixes synthesized in water and stabilized by at least one stabilizer such as sodium lauryl sulphate (SLS) or Gelatin, sodium tetradecyl sulfate (STS) or gelatin.

It is a further object of the present invention to provide almost pure HSA nanomatrixes synthesized in water.

It is a further object of the present invention to provide almost pure HSA nanomatrixes synthesized in water and stabilized by hemoglobin molecules.

It is a further object of the present invention to provide Hb and HSA nanomatrixes which have drugs or biological agents prebonded to the HSA or Hb molecules before formation of the nanomatrixes.

While the present invention discusses the synthesis of nanomatrixes from HSA) hemoglobin and gelatin, it is anticipated that any protein source, be it natural, modified natural or synthetic protein, such as immunoglobulins, myoglobins, enzymes, hormones, glycorylated-albumins, pyridoxylated-hemoglobins and polymerized hemoglobins, can all serve as appropriate protein sources for this process.

Further novel features and other objects of the present invention will become apparent from the following detailed description, discussion and the appended claims, taken in conjunction with the drawings.

DETAILED DESCRIPTION OF THE PREFERRED EMBODIMENT

Although specific embodiments of the present invention will now be described, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

The present invention differs from all prior arts in that no cross-linking agents or heat denaturation procedures are used. By avoiding the use of cross-linking agents or heat denaturation, the possibility of introducing new antigenicities to the biological material is avoided. New antigenicity may cause anaphylactic reactions to the hosts and is thus dangerous. All the prior art employ these undesirable methods because without them the microspheres will not form or will fall apart immediately upon the slightest perturbation of the synthetic media. It is a surprise finding of the present invention that stable nanomatrixes can be formed without cross-linking agents or heat denaturation procedures. The present invention results in nanomatrixes which are stable in the synthetic media, and do not redissolve after dilution or removal of the synthesis media in vitro or in vivo.

The present invention also allows microscopic particles, typically larger than 1micron in diameter, completely monodispersed with no aggregates, to be formed under ambient conditions by simple mixing of stable ingredient solutions. There are many advantages to such a method. Stable synthesis material can be stored separately and mixed only immediately before the nanomatrixes are to be synthesized. No elaborate machines are needed. When left undisturbed, the particles will settle by gravity without aggregation, which allows purification of massive quantities with economy.

These particles are called nanomatrixes to describe more conveniently their sizes. Most particles are larger than 1 micron in diameter; some are less than 50 nanometers. The particles do not have an enclosing membrane. The protein matrix is envisioned to be like a cotton ball which serve as scaffolds for biologically active molecules to bind to or be trapped therein. The porous nature of the structure allows the substrate of biologically active molecules to diffuse into the interior of the nanomatrix and for reaction products to diffuse out. Similarly, drugs can diffuse out of the nanomatrixes at rates dependent on the porosity of the nanomatrix carrier.

Since no cross-linking process or agents were used, it is expected that the nanomatrixes formed would easily be reversible or redissolvable upon dilution of the ingredient solutions. It is therefore a surprising finding that nanomatrixes can be formed which are stable for several days without redissolving or aggregation in different buffer solutions. The mechanism for prolonged stability of the nanomatrixes is not known. It is possible that upon assembly of the correct proportion of different molecules, certain hydrophobic regions are built up such that a greater stability is achieved with the nanomatrix than is possible with or anticipated from the individual molecules. An analogy would be the stability of an assembled jigsaw puzzle where individual pieces are inter-locked by their matching borders to generate stability for the whole puzzle. Another possibility is that the heme- group in the hemoglobin is unstable and becomes available for HSA binding. Since one HSA molecule can bind many molecules of heme, there exists the possibility of cross-affinity between the molecules However the mechanism must be more complex since (a) pure Hb in the absence of HSA can form nanomatrixes; (b) HSA saturated with hematin can still contribute to nanomatrix formation with Hb; and (c) nanomatrixes formed are not random in size or shape, but spherical and mono-dispersed.

Ideally, the nanomatrixes are formed from biocompatible proteins with low antigenicity. One such protein is human serum albumin (HSA) which is the body's natural material for binding drugs.

Another naturally occurring molecule of low antigenicity is hemoglobin (Hb). In addition to providing a porous structure for drug absorption, hemoglobin molecules can bind oxygen which is the drug of choice for many pathological conditions related to ischemia, such as coronary obstruction, cerebral vascular constriction, pulmonary vascular constriction, peripheral vascular disease and sickle cell crisis. It is only recently recognized that Hb molecules, when given in large amounts, may be toxic to the patient. With nanomatrixes, the great majority of Hb will not be in contact with the host's organs, except those Hb molecules exposed on the surface of the nanomatrixes. Therefore, nanomatrixes with a high Hb concentration can mimic erythrocytes and may be less toxic than soluble Hb to the host if used in massive amounts as oxygen carriers.

In addition, hemoglobin nanomatrixes can be made to carry bloodclot-dissolving agents such as urokinase or streptokinase. Injection of such dual function nanomatrixes into patients suffering from acute coronary spasm, thrombosis or embolism can have the advantage that some nanomatrixes (being about 0.1 micron small) will be able to navigate through the partial occlusion (which are probably several orders of magnitude larger in diameter) to deliver oxygen to the distal sites while other nanomatrixes retained by the blood clot will work on dissolving the clot to recannulate the coronary vessel.

EXPERIMENTS OF THE PRESENT INVENTION

Extensive amount of experiments have been performed in great detail for the study and research of the present invention. The following experiments have been performed to prove the validity of the present invention.

In the following experiments, stock hemoglobin (Hb) solutions were crystalline stroma-free human hemoglobin solution (approximately 60 mg/ml) maintained in a buffer containing at least 1.9 millimolar of potassium, 17 millimolar of sodium and 0.17% (w/v) of glucose; human serum albumin USP, (HSA), were purchased from pharmaceutical companies, typically as 250 mg/ml solutions in normal saline, which can be further diluted with other phosphate buffer or Tris, or HEPES buffers. Other reagents were typically dissolved and diluted in water unless otherwise specified, e.g. surfactant, sodium lauryl sulphate (SLS) and sodium tetradecyl sulphate (STS). It is anticipated that other suitable cationic, anionic and non-ionic surfactants may also be used.

The results of these experiments of the present invention have discovered the following important facts:

1) Increasing amounts of co-surfactant or desolubilizer used will increase the yield of nanomatrixes.

2) Under conditions where maximal yield is not desired, pure hemoglobin (Hb) nanomatrixes could be synthesized in a normal saline buffer but they are unstable and tend to aggregate together. Presence of human serum albumin (HSA) of approximately 4% (weight of HSA per total weight of protein) will provide stability to the primarily Hb nanomatrixes (about 96% of total protein mass). A higher HSA to hemoglobin ratio also resulted to form progressively smaller nanomatrixes.

3) Pure Hb nanomatrixes could be also synthesized in water but they are unstable and tend to aggregate together. Presence of at least one of the stabilizer such as sodium lauryl sulphate (STS) or Gelatin will provide stability to the primarily Hb nanomatrixes.

4) A higher gelatin to hemoglobin ratio resulted in smaller nanomatrixes. No significant difference in size was observed by using a higher HSA to hemoglobin ratio on nanomatrixes synthesized in butanol, but differences in size are observed by using a higher HSA to hemoglobin ratio on nanomatrixes synthesized in propanol.

5) Under conditions where an optimal amount of desolubilizer is used to produce maximal yield of nanomatrixes, pure Hb nanomatrixes can be produced which requires addition of a final concentration of 2.5 mg HSA/ml after appearance of turbidity in order to stabilize the product from aggregation.

6) Part of the 2.5 mg/ml HSA mentioned in 5) can be added to the protein solution before the addition of the alcohol, the balance amount of HSA can be added after the addition of the alcohol.

7) Higher concentrations of hemoglobin solution resulted in larger nanomatrixes, and at least 4.76 percent by weight of gelatin is needed for preventing aggregates occurring in synthesis of Hb nanomatrixes.

8) The absence of a stabilizer such as hemoglobin from HSA solution resulted nanomatrixes that can easily be reversed by dilution of reagents. However, inclusion of as little as 1.48% of hemoglobin will greatly increase the stability of the HSA nanomatrixes.

9) Substantially high concentration of surfactant resulted in larger HSA nanomatrix size, excessive surfactant even resulted in aggregates. When a critical amount of co-surfactant was exceeded by a small amount, the result was aggregated spheres instead of monodispersed nanomatrixes. The highest final concentration of non-dialyzed HSA (before addition of co-surfactant) that can produce monodispersed nanomatrixes is 148 mg/mi. With Dialyzed HSA the final concentration that can be used to produce monodispersed nanomatrixes may be higher. Also methanol tends to produce smaller spheres than ethanol. It may be possible that a low STS concentration such as 1.4 mg/ml in conjunction with methanol would produce useful nanomatrixes with final concentrations of dialyzed HSA even higher than 148 mg/ml. Different cosurfactants have different effects on the sizes of Hb and HSA nanomatrixes.

10) Hb and HSA nanomatrixes encapsulating drugs are stable. Also the biological agents prebonded to hemoglobin molecules can be incorporated into Hb nanomatrixes.

11) Biologically active molecules entrapped by Hb and HSA nanomatrixes can maintain their biological activities.

The following is a detailed description of the procedures and results of the experiments of the present inv

EXPERIMENT ONE

TITLE Synthesis of hemoglobin (Hb) nanomatrixes in normal saline buffer with human serum albumin (HSA) as stabilizer

EXPERIMENT

Various amounts of a standard concentration of reagents or a fixed amount of reagent of various concentrations were mixed in one test tube in room temperature as listed in Table 1. Then 0.75 ml isopropanol (PROH) from a second test tube was then added quickly to the first test tube (tube 1). Within 10 seconds of vigorous mixing of the contents of the two test tubes, turbidity appeared. Examination of the content of the suspension under phase contrast microscopy revealed monodispersed nanomatrixes in tube 1 to 5 with visually homogenous sizes, as listed in Table 1. No aggregates were seen except in tube 6, 79 8. The suspensions in tube 1 to 5 was stable in room temperature without aggregation for at least 4 days. No sedimentation or aggregation of nanomatrixes were observed during the four days in tube 1 to 5. In contrast, sediments were observed in tube 6, 7, 8 within hours of synthesis.

It is noted that the compositions which resulted in Tubes 2 through 5 have the following Hb:HSA weight ratio:

Tube 2: Hb:HSA ≈ 57:43
Tube 3: Hb:HSA ≈ 73:27
Tube 4: Hb:HSA ≈ 84:16
Tube 5: Hb:HSA ≈ 92:8

This is based on the following calculation from the data listed in TABLE 1:

(a) Weight of Hb:
  Tubes 2-5: 60 mg/ml × 0.225 ml = 13.5 mg
(b) Weight of HSA:
  Tube 2: 100 mg/ml × 0.1 ml = 10.0 mg
  Tube 3: 50 mg/ml × 0.1 ml = 5.0 mg
  Tube 3: 25 mg/ml × 0.1 ml = 2.5 mg
  Tube 4: 12 mg/ml × 0.1 ml = 1.2 mg
(c) Total Weight of Protein:
  Tube 2: 13.5 mg (Hb) + 10.0 mg (HSA) = 23.5 mg
  Tube 3: 13.5 mg (Hb) + 5.0 mg (HSA) = 18.5 mg
  Tube 4: 13.5 mg (Hb) + 2.5 mg (HSA) = 16.0 mg
  Tube 5: 13.5 mg (Hb) + 1.2 mg (HSA) = 14.7 mg
(d) Weight Ratio (Hb:HSA):
  Tube 2: 13.5/23.5:10.0/23.5 ≈ 57:43
  Tube 3: 13.5/18.5:5.0/18.5 ≈ 73:27
  Tube 4: 13.5/16.0:2.5/16.0 ≈ 84:16
  Tube 5: 13.5/14.7:1.2/14.7 ≈ 92:18

Therefore, the weight ratio of Hb:HSA is within the range of approximately 57:43 and 92:8.

Aliquots of the nanomatrix preparations were placed in separate dialysis bags and dialyzed against at least 100 fold in volume of normal saline to check the stability of nanomatrixes upon removal of the co-surfactant propanol (PROH). Surprisingly, the nanomatrixes synthesized in tube 1 to 5 remained intact without aggregation or dissolution even after four days of dialysis. In contrast, large aggregates were seen inside the dialysis bags containing material synthesized in tube 6 to 8 within one hour of synthesis.

CONCLUSION

Pure hemoglobin nanomatrixes (without presence of HSA) could be synthesized in a normal saline buffer but they are unstable and tend to aggregate together. Presence of more than 4% HSA (weight of HSA per total weight of protein) in the initial solution will provide stability to the primarily hemoglobin (about 96% of total protein mass, assuming an equal ratio of Hb to HSA molecules are incorporated into the nanomatrixes). A higher HSA to hemoglobin ratio also resulted to form progressively smaller nanomatrixes.

TABLE 1

| Tube | Hb 60 mg/ml | HSA 0.1 ml | NS | PROH | SIZE micron |
|---|---|---|---|---|---|
| 1 | 0.225 ml | 200 mg/ml | 2.675 ml | 0.75 ml | 0.8 |
| 2 | 0.225 ml | 100 mg/ml | 2.675 ml | 0.75 ml | 1.0 |
| 3 | 0.225 ml | 50 mg/ml | 2.675 ml | 0.75 ml | 1.2 |
| 4 | 0.225 ml | 25 mg/ml | 2.675 ml | 0.75 ml | 1.5 |
| 5 | 0.225 ml | 12 mg/ml | 2.675 ml | 0.75 ml | 1.5 |
| 6 | 0.225 ml | 6 mg/ml | 2.675 ml | 0.75 ml | 2 to 4 |
| 7 | 0.225 ml | 3 mg/ml | 2.675 ml | 0.75 ml | 2 to 4 |
| 8 | 0.225 ml | 0 mg/ml | 2.675 ml | 0.75 ml | 2 to 4 |

EXPERIMENT TWO

TITLE Synthesis of hemoglobin (Hb) nanomatrixes in low ionic strength buffer with sodium tetradecyl sulphate (STS) or gelatin as stabilizer

EXPERIMENT

Sotradecol 3% is a brand of sodium tetradecyl sulfate (STS) approved for intravenous injection by the Food and Drug Administration (FDA). At the 3% concentration, STS was irritable to veins. However, lower concentrations are acceptable. Gelatin solutions were prepared by dissolving gelatins in distilled water (2% w/v).

Reagents (hemoglobin stock solution, water, gelatin or STS) were mixed in a first test tube (e.g., tube 9) according to Table 2. Subsequently aliquots of alcohols, such as propanol (PROH), butanol (BUOH) or ethanol (ETOH), from a second test tube were added quickly to the contents of first test tube. Turbidity appeared within ten seconds and homogenous monodispersed nanomatrixes (typically less than 0.2 micron in diameter) were seen under phase microscopy in tubes 9 to 17. These suspensions were homogenous and stable for at least 8 days without formation of sediments or aggregations.

In contrast, large aggregates were seen with the unaided eye in tubes 18, 19, 20 demonstrating that at least one stabilizer (either STS or gelatin molecules) must be present for stable monodispersed nanomatrixes to form.

Aliquots of the contents of tube 9 to 20 were serially diluted (2-fold steps) in either distilled water or 5% HSA solution in normal saline (to simulate the intravascular environment) until the original suspension became at least 1000 less concentrated. After at least 1000 fold dilution in either water or 5% HSA solution in normal saline, the contents from all tubes (9 to 20) still appeared turbid, indicating that the nanomatrixes (whether monodispersed or in aggregates) were stable to dilution.

CONCLUSION

Pure hemoglobin nanomatrixes (without presence of HSA) could also be synthesized in water or hypotonic solutions but they are unstable and tend to aggregate together. Presence of at least one of the stabilizers (STS or Gelatin) will provide stability to the primarily hemoglobin nanomatrixes.

TABLE 2

| Tube | Hb 60 mg/ml | WATER | STS 2.8 mg/ml | GEL 20 mg/ml | PROH | ALCOHOL BUOH | ETOH |
|---|---|---|---|---|---|---|---|
| 9 | 0.225 ml | 2.525 ml | 0.25 ml | none | none | none | 1.10 ml |
| 10 | 0.225 ml | 2.525 ml | 0.25 ml | none | none | 0.20 ml | none |
| 11 | 0.225 ml | 2.525 ml | 0.25 ml | none | 1.00 ml | none | none |
| 12 | 0.225 ml | 2.675 ml | none | 0.1 ml | none | none | 1.25 ml |
| 13 | 0.225 ml | 2.675 ml | none | 0.1 ml | none | 0.20 ml | none |
| 14 | 0.225 ml | 2.675 ml | none | 0.1 ml | 0.75 ml | none | none |
| 15 | 0.225 ml | 2.425 ml | 0.25 ml | 0.1 ml | none | none | 1.23 ml |
| 16 | 0.225 ml | 2.425 ml | 0.25 ml | 0.1 ml | none | 0.20 ml | none |
| 17 | 0.225 ml | 2.425 ml | 0.25 ml | 0.1 ml | 1.00 ml | none | none |
| 18 | 0.225 ml | 2.775 ml | none | none | none | none | 1.20 ml |
| 19 | 0.225 ml | 2.775 ml | none | none | none | 0.20 ml | none |
| 20 | 0.225 ml | 2.775 ml | none | none | 0.75 ml | none | none |

EXPERIMENT THREE

TITLE Effect of a higher stabilizer molecule to hemoglobin (Hb) ratio on synthesis of nanomatrixes

EXPERIMENT

Reagents were again mixed in a first test tube (e.g., tube 21) as listed in Table 3 and subsequently 0.3 ml of butanol (BUOH) was added from a second test tube to produce turbidity.

The sizes of nanomatrixes formed are also shown in Table 3. The nanomatrixes were homogenous in size for each preparation and stable to dilution to over 100x in distilled water.

CONCLUSION

A higher gelatin to hemoglobin ratio resulted in smaller nanomatrixes. However, no significant difference in size was observed by using a higher HSA to hemoglobin ratio on nanomatrixes synthesized in butanol (BUOH), as compared to the result from Experiment One as shown in Table 1, where a higher HSA to hemoglobin ratio resulted in progressively smaller nanomatrixes (tube 1 to 5) when formed in propanol (PROH).

EXPERIMENT FOUR

TITLE Effect of a higher concentration of hemoglobin (Hb) on synthesis of nanomatrixes

EXPERIMENT

The concentration of hemoglobin molecules has been increased in tubes 27–29, as shown in Table 4. As a result, monodispersed nanomatrixes were observed with average size of 1.0 to 1.2 microns in diameter.

CONCLUSION

Higher concentrations of hemoglobin solution resulted in larger nanomatrixes.

TABLE 4

| Tube | Hb 60 mg/ml | WATER | STS 2.8 mg/ml | HSA 250 mg/ml | ALCOHOL BUOH |
|---|---|---|---|---|---|
| 27 | 2.25 ml | 0.40 ml | 0.25 ml | 0.10 ml | 0.30 ml |
| 28 | 2.25 ml | 0.25 ml | 0.25 ml | 0.25 ml | 0.30 ml |
| 29 | 2.25 ml | 0.00 ml | 0.25 ml | 0.50 ml | 0.30 ml |

EXPERIMENT FIVE

TITLE Synthesis of human serum albumin (HSA) nanomatrixes

EXPERIMENT

Stock HSA solutions (25% in normal saline) were diluted in distilled water to 80 mg/ml. Aliquots of this diluted HSA were mixed with various amounts of sodium lauryl sulphate (SLS) and distilled water as listed in Table 5. Subsequently 0.8 ml of ethanol (ETOH) was added. Only the minimal amount that is needed to produce turbidity is used. Excessive amounts of alcohol will lead to aggregation of nanomatrixes. Upon dilution with distilled water or normal saline buffer (1 vol to 1

TABLE 3

| Tube | Hb 60 mg/ml | WATER | STS 2.8 mg/ml | GEL 20 mg/ml | HSA 250 mg/ml | ALCOHOL BUOH |
|---|---|---|---|---|---|---|
| 21 | 0.225 ml | 2.425 ml | 0.25 ml | 0.10 ml | none | 0.30 ml |
| 22 | 0.225 ml | 2.175 ml | 0.25 ml | 0.25 ml | none | 0.30 ml |
| 23 | 0.225 ml | 1.925 ml | 0.25 ml | 0.50 ml | none | 0.30 ml |
| 24 | 0.225 ml | 2.425 ml | 0.25 ml | none | 0.10 ml | 0.30 ml |
| 25 | 0.225 ml | 2.175 ml | 0.25 ml | none | 0.25 ml | 0.30 ml |
| 26 | 0.225 ml | 1.925 ml | 0.25 ml | none | 0.50 ml | 0.30 ml |

| Tube | SIZE |
|---|---|
| 21 | 0.1 micron |
| 22 | ≈0.05 micron |
| 23 | <<0.05 micron, hard to see under 1000× microscopy |
| 24 | 0.2 micron |
| 25 | 0.15 micron |
| 26 | 0.2 micron | vol), the contents of tubes 30 and 31 redissolved into a clear solution within one hour. It was also observed that aggregates had occurred in tube 32.

CONCLUSION

Absence of a stabilizer such as hemoglobin from HSA solution resulted in nanomatrixes that can easily redissolve on dilution of the co-surfactant ETOH, such as occurred in tubes 30 and 31. Absence of a suitable surfactant such as SLS results in useless aggregates, such as occurred in tube 32.

TABLE 5

| Tube | HSA 80 mg/ml | WATER | SLS 8 mg/ml | ETOH | SIZE |
|---|---|---|---|---|---|
| 30 | 0.25 ml | 0.500 ml | 0.250 ml | 0.8 ml | 0.1 μm |
| 31 | 0.25 ml | 0.625 ml | 0.125 ml | 0.8 ml | 0.05 μm |
| 32 | 0.25 ml | 0.750 ml | 0.000 ml | 0.8 ml | aggr. |

EXPERIMENT SIX

TITLE Reversibility of human serum albumin (HSA) nanomatrixes synthesized in the presence of a small amount of hemoglobin (Hb) as stabilizer

EXPERIMENT

Stock hemoglobin solutions were diluted to 3 mg/ml with distilled water and added to a first test tube in the presence of STS (e.g., tube 33) as indicated in Table 6. Subsequently, a minimal amount of ethanol (ETOH) was used to cause turbidity. The turbid suspension was added into dialysis bags to be dialyzed against at least 100 fold of normal saline to remove the reagents including ethanol. Only tube 33 turned clear within 2 hours. The contents of tube 34 to 37 remain turbid for 3 more days of dialysis.

CONCLUSION

Inclusion of as little as 1.48% (0.3 divided by 20+0.3 mg total protein) of hemoglobin in the initial mixture will greatly increase the stability of the HSA nanomatrixes.

TABLE 6

| Tube | HSA 80 mg/ml | Hb 3 mg/ml | WATER | STS 8 mg/ml | ETOH |
|---|---|---|---|---|---|
| 33 | 0.25 ml | 0.0 ml | 0.5 ml | 0.25 ml | 0.8 ml |
| 34 | 0.25 ml | 0.1 ml | 0.4 ml | 0.25 ml | 0.8 ml |
| 35 | 0.25 ml | 0.2 ml | 0.3 ml | 0.25 ml | 0.4 ml |
| 36 | 0.25 ml | 0.3 ml | 0.2 ml | 0.25 ml | 0.3 ml |
| 37 | 0.25 ml | 0.4 ml | 0.1 ml | 0.25 ml | 0.2 ml |

EXPERIMENT SEVEN

TITLE Entrapment of drugs with human serum albumin (HSA) nanomatrixes

EXPERIMENT

Doxorubin (ADR) was purchase from Adria and reconstituted with water to a final concentration of 0.3 mg/ml. A stable solution was prepared by mixing 0.10 ml or 0.25 ml of HSA (at 80 mg/ml, diluted with water) with various volumes of STS (8 mg/ml with water) and 0.25ml of doxorubicin solution (0.3 mg/ml with water), with or without hemoglobin (Hb). Subsequently, an aliquot of ethanol (ETOH) or propanol (PROH) was added with rapid shaking to mix them well. Red nanomatrixes were observed in preparations without hemoglobin (tube 103, 104, 105, 106) which redissolves within one hour to a clear red solution (color of ADR solutions) after dilution with an equal part of distilled water or normal saline buffer. Red nanomatrixes prepared with hemoglobin with an adequate amount of HSA (tube 101, 102) stayed intact after dilution with an equal part of distilled water or normal saline buffer for up to at least 24 hours.

CONCLUSION

Hb and HSA nanomatrixes containing encapsulated drugs are stable with various degrees of reversibility. Although ADR is used here, other biological active molecules can similarly be incorporated such as receptor analogs (e.g., recombinant CD4), receptor agonist or antagonist, inhibitors, stimulants, growth factors, hormones, cytokines, glycosylated proteins, aminoacid, carbohydrates, RNA, DNA, anti-sense polynucleotides polymerases, viruses, lipids, steroids and ribozymes. Biologically interactive components, which may be by themselves inert but useful to biological systems, such as contrast dye and air bubbles, may also be incorporated by this method.

TABLE 7

| Tube | Hb 63 mg/ml | HSA 80 mg/ml | STS 8 mg/ml | WATER | ADR 0.3 mg/ml | ALCOHOL PROH |
|---|---|---|---|---|---|---|
| 101 | 0.25 ml | 0.1 ml | 0.1 ml | 0.15 ml | 0.25 ml | 0.20 ml |
| 102 | 0.25 ml | 0.1 ml | 0.0 ml | 0.25 ml | 0.25 ml | 0.35 ml |
| | | | | | | ETOH |
| 103 | none | 0.25 ml | 0.25 ml | 0.25 ml | 0.25 ml | 0.80 ml |
| 104 | none | 0.25 ml | 0.20 ml | 0.30 ml | 0.25 ml | 0.80 ml |
| 105 | none | 0.25 ml | 0.15 ml | 0.35 ml | 0.25 ml | 0.80 ml |
| 106 | none | 0.25 ml | 0.10 ml | 0.40 ml | 0.25 ml | 0.80 ml |

EXPERIMENT EIGHT

TITLE Preparation of radioactive hemoglobin (.Hb) nanomatrixes with alkaline phosphatase (AK) enzyme activity

EXPERIMENT

The purpose of the experiment was to find out if biological agents prebonded to hemoglobin molecules can be incorporated into Hb nanomatrixes. Radioactive iodine was chosen because its activity could easily be measured with a gamma counter.

An additional enzyme, alkaline phosphatase (AK), was added to the mixture to see if it could be incorporated into the nanomatrix and if so, whether enzymatic activity was preserved. The activity of AK could easily be measured and would serve as a model for other drugs such as enzymes (e.g., urokinase) or protein antibiotics (polymyxin), or biological molecules such as antibodies, growth factors, hormones (e.g. insulin) and cytokines (e.g., interleukins, interferons, tumor necrosis factor, prostaglandin, granulocyte-macrophage colony-stimulating factor).

An aliquot of hemoglobin solution was first iodinated with Iodine 125 by using standard chloramine-T linking method. The specific activity of the labeled hemoglobin solution was found to be approximately 6 microcurie per mg protein. The conditions of tube 2 in Experiment One (shown in Table 1) was used except that radioactive hemoglobin molecules were premixed with the nonradioactive hemoglobin solution to result in a final concentration of 60 mg/ml of radioactive hemoglobin of which 0.225 ml was used for synthesis of the nanomatrixes. Instead of normal saline buffer, a solution of alkaline phosphatase (0.1 mg/ml in normal saline buffer) was used.

After formation of nanomatrixes with the addition of 0.8 ml propanol (PROH), an aliquot was used to measure its radioactivity and AK activity. Another aliquot was centrifuged to remove all the nanomatrixes. The clear supernatant was subsequently assayed for its radioactivity and AK activity. It was found that at least 80 percent of the total radioactivity as well as AK activity resided with the nanomatrix.

CONCLUSION

The biological agents prebonded to hemoglobin molecules can be incorporated into Hb nanomatrixes. Biologically active molecules can be trapped within the relatively stable nanomatrixes and retain their biological activities.

EXPERIMENT NINE

TITLE Lowest amount of gelatin needed as stabilizer for synthesis of hemoglobin (Hb) nanomatrixes in hyperosmolar buffer

EXPERIMENT

Reagents were mixed in first test tube (e.g., tube 38) as listed in Table 8. Buffer used contained 3x normal saline (i.e. 465 millimolar NACI) with 20 millimolar sodium phosphate (pH 7.4), dissolved in water (total osmolarity equal to at least 970 milliosmos).

Radioactive hemoglobin (radiolabeled with iodine-125 purchased from commercial source) was added to stock nonradioactive hemoglobin solution to generate a mixture with radioactivity of about 5,000 cpm per mg hemoglobin.

After equilibration for at least 5 minutes, about 1.12 ml of butanol (BUOH) was added to each tube and the contents well shaken. Aliquots from the resultant turbid suspensions were examined under phase microscopy. All preparations from tube 38 to 42 contained monodispersed nanomatrixes about 0.05 micron in diameter. In contrast, tube 43 to 45 contained aggregates of nanomatrixes.

The percentage of radioactive hemoglobin molecules that were incorporated into the nanomatrixes were calculated as follows:

1) Radioactivity from aliquots of suspensions were counted in a gamma counter to obtain cpm per ml of suspension.

2) Nanomatrixes were removed by centrifugation in high speed for at least 20 minutes.

3) Radioactivity from respective aliquots of the clear supernatant were counted.

4) Differences between cpm per ml of whole suspension and that of the supernatant equals the cpm of nanomatrixes originally suspended in one ml of suspension.

5) The Percentage yield =cpm of nanomatrixes obtained from one ml of suspension divided by cpm of the one ml of original suspension.

6) The yield of nanomatrixes ranged from 73% to 95%.

Aliquots of the contents from tube 38 to 45 were placed in dialysis bags and dialyzed in over 100 fold normal saline to test the integrity of the nanomatrixes. It was noticed that tube 38 to 42 had no aggregation for at least four days, while aggregates were visible to the unaided eye for contents from tube 43 to 45 within one hour of dialysis.

Dilution of one volume of the aliquots from tube 38 to 45 with two volumes of water to produce a final concentration of sodium chloride equivalent to normal saline buffer showed that the nanomatrixes produced in tube 38 to 45 were all stable in normal saline buffer except that those from tube 38 to 42 remained as monodispersed nanomatrixes and those from 43 to 45 remained aggregated.

CONCLUSION

More than 3.6 percent by weight of gelatin in the initial solution is needed for preventing aggregates occurring in synthesis of Hb nanomatrixes. Assuming equal proportions of Hb and gelatin are incorporated into nanomatrixes, this experiment suggests that more than 3.6% of total weight of protein should be gelatin to maintain monodispersity of primarily Hb nanomatrixes.

TABLE 8

| Tube | Hb 50 mg/ml | BUFFER | STS 3.2 mg/ml | GEL 10 mg/ml | BUOH |
|---|---|---|---|---|---|
| 38 | 0.80 ml | 8.20 ml | 1.0 ml | 1.00 ml | 1.12 ml |
| 39 | 0.80 ml | 8.40 ml | 1.0 ml | 0.80 ml | 1.12 ml |
| 40 | 0.80 ml | 8.60 ml | 1.0 ml | 0.60 ml | 1.12 ml |
| 41 | 0.80 ml | 8.80 ml | 1.0 ml | 0.40 ml | 1.12 ml |
| 42 | 0.80 ml | 9.00 ml | 1.0 ml | 0.20 ml | 1.12 ml |
| 43 | 0.80 ml | 9.05 ml | 1.0 ml | 0.15 ml | 1.12 ml |
| 44 | 0.80 ml | 9.10 ml | 1.0 ml | 0.10 ml | 1.12 ml |
| 45 | 0.80 ml | 9.20 ml | 1.0 ml | 0.00 ml | 1.12 ml |

EXPERIMENT TEN

TITLE Effect of surfactant concentration on synthesis of human serum albumin (HSA) nanomatrixes

EXPERIMENT

As shown in Table 9, 2.5 ml of sodium lauryl sulphate (SLS) of various concentrations were mixed with 2.5 ml of HSA (60 mg/ml diluted in water). After 5 minutes of equilibration, 5.5 ml of ethanol (ETOH) was added to each tube.

Aliquots of the contents from tubes 46 to 48 were examined under phase microscopy. It was noted that tube 46 and 47 contained monodispersed nanomatrixes whereas tube 48 contained useless aggregates consisting of thousands of spheres each 1.5 to 2 microns in diameter.

CONCLUSION

Substantially high concentration of surfactant resulted in larger HSA nanomatrix size, even aggregates.

TABLE 9

| Tube | HSA 60 mg/ml | SLS 2.5 ml | ETOH | SIZE micron |
|---|---|---|---|---|
| 46 | 2.5 ml | 6 mg/ml | 5.5 ml | 0.8 |
| 47 | 2.5 ml | 10 mg/ml | 5.5 ml | 1.2 |
| 48 | 2.5 ml | 14 mg/ml | 5.5 ml | aggregates of 1.5 to 2 micron spheres |

EXPERIMENT ELEVEN

TITLE Effect of the concentration of surfactant on synthesis of hemoglobin (Hb) nanomatrixes

EXPERIMENT

Hemoglobin solutions (30 mg/mi) were mixed with 0.1 ml of various concentrations of sodium lauryl sulphate (SLS) as shown in Table 10. Subsequently 0.35 ml of ethanol (ETOH) was added to the 1.1 mi of mixture and shaken to produce turbidity.

CONCLUSION

Again the concentration of surfactant is important. Increasing concentrations lead to larger nanomatrixes, even aggregations.

TABLE 10

| Tube | HSA 30 mg/ml | SLS 0.1 ml | ETOH | SIZE micron |
|---|---|---|---|---|
| 49 | 1.0 ml | 7 mg/ml | 0.35 ml | 0.1 |
| 50 | 1.0 ml | 9 mg/ml | 0.35 ml | 0.2 |
| 51 | 1.0 ml | 11 mg/ml | 0.35 ml | aggregates of 0.3 micron spheres |

EXPERIMENT TWELVE

TITLE Effect of increasing amounts of co-surfactant on synthesis of hemoglobin (Hb) and human serum albumin (HSA) nanomatrixes

EXPERIMENT

Reagents were mixed in tubes (e.g., tube 52) as listed in Table 11. Subsequently, 0.50 to 0.66 ml of ETOH was added to the tubes.

CONCLUSION

When a critical amount of co-surfactant was exceeded by a small amount, the result was aggregated spheres instead of monodispersed nanomatrixes.

TABLE 11

| Tube | Hb 63 mg/ml | HSA 250 mg/ml | SLS 9 mg/ml | ETOH | SIZE micron |
|---|---|---|---|---|---|
| 52 | 1 ml | 0.2 ml | 0.12 ml | 0.50 ml | <0.1 |
| 53 | 1 ml | 0.2 ml | 0.12 ml | 0.55 ml | 0.1 |
| 54 | 1 ml | 0.2 ml | 0.12 ml | 0.58 ml | 0.1 |
| 55 | 1 ml | 0.2 ml | 0.12 ml | 0.62 ml | 0.2 |
| 56 | 1 ml | 0.2 ml | 0.12 ml | 0.66 ml | small aggregates |

EXPERIMENT THIRTEEN

TITLE Effect of osmolariiy (hypotonicity) on synthesis of human serum albumin (HSA) nanomatrixes

EXPERIMENT

Standard HSA solutions with HSA dissolved in normal saline buffer were diluted with water and mixed with an equal volume of a suitable concentration of surfactant. After equilibration, a minimum amount of methanol was added quickly with shaking of the tube to produce turbidity. Non-dialyzed standard HSA solutions were used with Ethanol as well.

Dialyzed HSA were previously dialyzed extensively with distilled water before an equal volume of surfactant was added. After equilibration, a minimum amount of methanol was added with shaking to produced turbidity.

Ethanol was also used on non-dialyzed as well as dialyzed HSA solutions to see if the effects of low osmolarity were applicable with ETOH as co-surfactant.

The results are displayed in the following tables:
Table 12: Using non-dialyzed HSA with Methanol.
Table 13: Using dialyzed HSA with Methanol.
Table 14: Using non-dialyzed HSA with Ethanol.
Table 15: Using dialyzed HSA with Ethanol.

In all the Tables 12-15, the column labels appearing in the top horizontal list are the concentrations of STS (mg/ml, dissolved in water) immediately before addition of co-surfactant, and the row labels appearing in the left vertical list are concentrations of HSA (mg/ml) immediately before the addition of co-surfactant.

CONCLUSION

These experiments are designed in such a way that upon dilution of the non-dialyzed stock HSA solution with distilled water, the concentration of HSA as well as sodium chloride-containing solvent were equally and proportionally diluted. In Table 12, as the concentration of HSA reached down to 46 mg/ml, the sodium concentration was approximately $(150 \times 46/250)$ or 27.6 milliequivalent. Even at such a low osmolarity, no useful nanomatrixes were formed with the wide range of STS concentration used in conjunction with methanol as co-surfactant. In contrast, by using HSA extensively dialyzed in water to remove practically all free sodium ions, useful nanomatrixes were obtained (Table 13) at HSA concentration as high as 110 mg/ml in conjunction with STS concentration of 7.7 mg/ml. Again, the adverse effect of higher concentration of STS than optimal was observed. Similarly dialyzed HSA in conjunction with STS at concentration of 11.5 mg/mi produced useless aggregates.

When the experiments were repeated using ethanol as co-surfactant, the highest concentration of HSA that could result in monodispersed nanomatrixes was 148 mg/ml, in conjunction with STS concentration as low as 1.4 mg/ml (Table 14). Again, higher than optimal concentration of STS (e.g., 7.4 mg/ml) resulted in useless aggregates.

Attempts to repeat the effects of high concentrations of dialyzed HSA was hampered by the fact that the stock HSA (non-dialyzed) solution became inevitably diluted with water during dialysis. Table 15 showed, however, that nanomatrixes of extremely small sizes could be obtained from dialyzed HSA up to the concentration of 110 mg/mi in conjunction with STS concentration of 2.3 mg/ml. Too low (0.8 mg/ml) or too high (e.g., 7.4 mg/ml) concentration of STS resulted in useless aggregates. Concentration of dialyzed HSA above 148 mg.ml (if available) will probably produce useful nanomatrixes also.

These experiments showed the complexity of various conditions that must be within narrow ranges for useful nanomatrix production. For example, low ionic strength (e.g., dialyzed HSA) allows a higher concentration of HSA to be used (compare Table 12 with 13). However, STS concentrations must be within a narrow range. The effect of co-surfactant was also obvious: using non-dialyzed HSA, methanol produced no useful nanomatrixes at STS concentration as low as 2.7 mg/ml and HSA concentration as low as 74 mg/mi (Table 12). However, ethanol produced useful nanomatrixes at HSA concentrations up to 148 mg/ml in conjunction with STS of 1.4 mg/ml (Table 14). In general methanol produced nanomatrixes smaller than ethanol.

TABLE 12

| HSA (mg ml) | STS (mg/ml in water) | | | | | | |
|---|---|---|---|---|---|---|---|
| | 11.5 | 7.3 | 6.4 | 5.5 | 4.5 | 3.6 | 2.7 |
| 110 | X | X | X | X | X | X | X |
| 102 | X | | | | | | |
| 92 | X | X | X | X | X | X | X |
| 83 | X | | | | | | |
| 74 | X | X | X | X | X | X | X |
| 64 | X | | | | | | |
| 55 | X | | | | | | |
| 46 | X | | | | | | |

X = Useless aggregates

TABLE 13

| HSA (mg/ml) | STS (mg/ml in water) | | | | | | | | | |
|---|---|---|---|---|---|---|---|---|---|---|
| | 11.5 | 9.1 | 8.2 | 7.7 | 7.3 | 6.4 | 5.5 | 4.5 | 3.6 | 2.7 |
| 110 | X | | C | | | | | | | |
| 102 | X | | C | | | | | | | |
| 92 | X | | X | | | | | | | |
| 83 | X | | D | | | | | | | |
| 74 | X | X | X | X | X | D | X | D | D | D |
| 64 | X | | C | | | | | | | |
| 55 | X | | C | | | | | | | |
| 46 | X | | C | | | | | | | |

C = Less than 0.05 micron spheres
D = Less than 0.1 micron spheres
X = Useless aggregates

TABLE 14

| HSA (mg/ml) | STS (mg/ml in water) | | | | | | | | | | |
|---|---|---|---|---|---|---|---|---|---|---|---|
| | 24.5 | 18.2 | 13.6 | 9.1 | 7.4 | 5.5 | 3.6 | 1.8 | 1.4 | 0.9 | 0 |
| 227 | X | X | X | X | X | X | X | X | X | X | |
| 216 | | | | | | | | | X | | |
| 204 | | | | | | | | | X | | |
| 193 | | | | | | | | | X | | |
| 185 | | | | | X | | | | | | |
| 182 | | | | | | | | | X | | |
| 170 | | | | | | | | | X | | |
| 159 | | | | | | | | | X | | |
| 148 | | | | | | | | | B | | |
| 136 | | | | | X | | | | B | | |
| 125 | | | | | | | | | B | | |
| 113 | | | | | | | | | B | | |
| 102 | | | | | | | | | B | | |
| 91 | | | | | X | | | | B | | |
| 79 | | | | | | | | | B | | |
| 74 | | | | | | | | A | | | |
| 56 | | | | | | | | A | | | |
| 37 | | | | | | | | B | | | |

A = 0.5 to 8 micron spheres
B = 1 to 2 micron spheres
X = Useless aggregates

TABLE 15

| HSA (mg/ml) | STS (mg/ml in water) | | | | | | | | | | |
|---|---|---|---|---|---|---|---|---|---|---|---|
| | 9.1 | 8.2 | 7.4 | 6.4 | 5.5 | 4.5 | 3.6 | 2.7 | 2.3 | 1.4 | 0.8 |
| 110 | | | | | | | | | H | F | X |
| 101 | | | | | | | | | E | E | X |
| 92 | | | | | | | | | G | H | X |
| 83 | | | | | | | | | G | H | X |
| 74 | X | X | X | E | F | F | G | G | E | E | X |
| 64 | | | | | | | | | I | H | X |

E = 0.1 micron spheres
G = 0.3 to 0.5 micron spheres
H = Less than 0.05 micron spheres
I = 0.8 to 1 micron spheres
X = Useless aggregates

EXPERIMENT FOURTEEN

TITLE Effect of co-surfactant on synthesis of hemoglobin (Hb) and human serum albumin (HSA) nanomatrixes

EXPERIMENT

Reagents were mixed in first tube in accordance with Table 16. After equilibration, 0.15 ml of the respective alcohol was added and the tubes were immediately shaken to produce turbidity.

Examination of an aliquot of the content from tube 57, 58 and 59 showed monodispersed nanomatrixes of sizes 0.05, 0.5 and 1.5 micron respectively.

CONCLUSION

Different co-surfactants have different effects on the sizes of Hb and HSA nanomatrixes.

TABLE 16

| Tube | Hb 60 mg/ml | HSA 250 mg/ml | STS 30 mg/ml | ETOH | ALCOHOL PROH | BUOH | SIZE micron |
|---|---|---|---|---|---|---|---|
| 57 | 1.0 ml | 0.12 ml | 0.112 ml | 0.462 ml | none | none | 0.05 |
| 58 | 1.0 ml | 0.12 ml | 0.112 ml | none | 0.462 ml | none | 0.5 |
| 59 | 1.0 ml | 0.12 ml | 0.112 ml | none | none | 0.462 ml | 1.5 |

EXPERIMENT FIFTEEN

TITLE Synthesizing stable nanomatrixes larger than 1 micron in diameter under high yield conditions

EXPERIMENT

Hb and HSA were dissolved in normal saline to result in concentrations of 5 mg/ml and 2.5 mg/ml, respectively, in a series of 8 tubes. To each tube was added 0.6, 0.8, 1.0, 1.2, 1.4, 1.6, 1.8, 2.0 ml of n-Butanol, respectively, per 10 ml of the protein mixture solution. The tubes were thoroughly shaken to produce turbidity. After one hour, 5 ml of the nanomatrixes suspension was removed, and centrifuged to obtain the nanomatrix pellet. After removing the supernatant without disturbing the pellet, 5ml of 0.05 N Sodium hydroxide was added to the pellet to solubilize completely the pellet for protein analysis. The amount of Hb obtained from the pellet as a percentage of the amount of soluble Hb present before addition of the alcohol was defined as the "yield" of nanomatrixes for the experimental condition. It was found that the yield of nanomatrixes increased with increasing amount of butanol used, with the yield reaching to about 95% when the ratio (v/v) of butanol to protein solution was 0.14. The yield obtained with a higher ratio of alcohol to protein volume ratio is similar. Therefore, a ratio of 0.14 ml butanol per ml protein solution was used subsequently to test conditions suitable for production of large protein particles which are stable and which can be produced with high yields.

Reagents (Hb and HSA) were mixed in tube 60 to tube 99, in accordance with Table 17 to see what kind of nanomatrixes will be produced with various HSA concentrations, either premixed with Hb or added after formation of nanomatrixes. After 0.14 ml of butanol was added to 1 ml of protein mixture, the tubes were capped and shaken upside down for three to ten times to produce turbidity.

It was noted when the concentration of HSA was less than 2.5 mg/ml in the solution containing the first and second protein (with Hb approximately 5 mg/ml), the nanomatrixes synthesized were initially monodispersed but tend to stick to form aggregates within minutes after their formation. However, if an additional "stabilizing solution" of HSA was added immediately after the appearance of turbidity, to bring the total concentration of HSA in the suspension to more than 2.5 mg/ml, the nanomatrixes would not aggregate and were stable to subsequent washing or centrifugation without aggregation.

This observation suggests that under these conditions of synthesis to obtain high yields with a high alcohol to protein solution (v/v) ratio, there is a period of less than 10 minutes of instability (if the HSA present is less than 2.5 mg/ml) and a certain minimum amount of HSA (added after formation of the nanomatrixes) can still adhere to the surface of the nanomatrixes to produce subsequent stability and non-aggregation of nanomatrixes. This suggests also that biologically active molecules which can be used as "homing devices" (e.g. antibodies and ligands against certain cell receptors) can be added during this relatively unstable (with respect to aggregation) period so that they will not be buried in the interior of the matrix but will remain on the surface to be effective against their targets.

Examination of an aliquot of the content from tube 60 to 99 showed nanomatrixes with diameters listed on table 17.

Nanomatrixes settle to the bottom of the tube within one day after which the supernatants can be removed by suction and the nanomatrixes can be washed several times with either normal saline or distilled water. Examination under phase contrast microscopy showed that the size of the nanomatrixes have not changed and nanomatrixes are stable without redissolving.

CONCLUSION

Under the maximal conditions of synthesis for obtaining high yields with a high alcohol to protein solution (v/v) ratio, a certain minimum amount of HSA can still adhere to the surface of the nanomatrixes to produce subsequent stability and non-aggregation of nanomatrixes. The biologically active molecules can also be added during this relatively unstable period so that they will not be buried in the interior of the matrix but will remain on the surface to be effective against their targets.

TABLE 17

| Tube | Hb 30 mg/ml | HSA 25 mg/ml | NS | BUOH | Stablizing HSA 25 mg/ml (Volume in microliters) | Size micron |
|---|---|---|---|---|---|---|
| 60 | 16.7 | 0 | 983.3 | 140 | 0 | aggregation |
| 61 | 16.7 | 20 | 963.3 | 140 | 0 | aggregation |
| 62 | 16.7 | 50 | 933.3 | 140 | 0 | 1 |
| 63 | 16.7 | 100 | 883.3 | 140 | 0 | 0.8 |
| 64 | 16.7 | 200 | 783.3 | 140 | 0 | 0.4 |
| 65 | 16.7 | 0 | 983.3 | 140 | 100 | 1 |
| 66 | 16.7 | 20 | 963.3 | 140 | 80 | 1 |
| 67 | 16.7 | 50 | 933.3 | 140 | 50 | 0.8 |
| 68 | 16.7 | 100 | 833.3 | 140 | 0 | 0.8 |
| 69 | 16.7 | 200 | 783.3 | 140 | 0 | 0.4 |
| 70 | 66.7 | 0 | 933.3 | 140 | 0 | aggregation |
| 71 | 66.7 | 20 | 913.3 | 140 | 0 | aggregation |
| 72 | 66.7 | 50 | 883.3 | 140 | 0 | 1.5–2.0 |
| 73 | 66.7 | 100 | 833.3 | 140 | 0 | 1.2–1.5 |
| 74 | 66.7 | 200 | 733.3 | 140 | 0 | 1 |
| 75 | 66.7 | 0 | 933.3 | 140 | 100 | 2 |
| 76 | 66.7 | 20 | 913.3 | 140 | 80 | 1–2.5 |
| 77 | 66.7 | 50 | 883.3 | 140 | 50 | 1.0–1.5 |
| 78 | 66.7 | 100 | 833.3 | 140 | 0 | 1 |
| 79 | 66.7 | 200 | 733.3 | 140 | 0 | 1 |
| 80 | 166.7 | 0 | 833.3 | 140 | 0 | aggregation |
| 81 | 166.7 | 20 | 813.3 | 140 | 0 | aggregation |
| 82 | 166.7 | 50 | 783.3 | 140 | 0 | aggregation |
| 83 | 166.7 | 100 | 733.3 | 140 | 0 | 2.0–2.5 |
| 84 | 166.7 | 200 | 633.3 | 140 | 0 | 2.0–2.5 |
| 85 | 166.7 | 0 | 833.3 | 140 | 100 | 2–4 |
| 86 | 166.7 | 20 | 813.3 | 140 | 80 | 2–4 |
| 87 | 166.7 | 50 | 783.3 | 140 | 50 | 2–3 |
| 88 | 166.7 | 100 | 733.3 | 140 | 0 | 2–2.5 |
| 89 | 166.7 | 200 | 633.3 | 140 | 0 | 2–2.5 |
| 90 | 333.3 | 0 | 666.7 | 140 | 0 | aggregation |
| 91 | 333.3 | 20 | 646.7 | 140 | 0 | aggregation |
| 92 | 333.3 | 50 | 616.7 | 140 | 0 | aggregation |
| 93 | 333.3 | 100 | 566.7 | 140 | 0 | aggregation |
| 94 | 333.3 | 200 | 466.7 | 140 | 0 | aggregation |
| 95 | 333.3 | 0 | 666.7 | 140 | 100 | aggregation |

TABLE 17-continued

| Tube | Hb 30 mg/ml | HSA 25 mg/ml | NS | BUOH | Stablizing HSA 25 mg/ml | Size micron |
|---|---|---|---|---|---|---|
| | | | | | (Volume in microliters) | |
| 96 | 333.3 | 20 | 646.7 | 140 | 80 | aggregation |
| 97 | 333.3 | 50 | 616.7 | 140 | 50 | aggregation |
| 98 | 333.3 | 100 | 566.7 | 140 | 0 | aggregation |
| 99 | 333.3 | 200 | 466.7 | 140 | 0 | aggregation |

EXPERIMENT SIXTEEN

TITLE Location of biologically active molecules in nanomatrixes

EXPERIMENT

Reagents were mixed in a first tube as in Tube 87 of Experiment 15 except that instead of 0.7833 ml of normal saline, 0.7833ml of an alkaline phosphatase enzyme solution (1 mg per ml, dissolved in normal saline) was used. In addition, the "stabilizing protein solution" consists of Hemagglutinin molecules (Fluogen, 0.58 mg/ml concentration.)

After allowing the nanomatrixes to settle to the bottom of the tube, the supernatant was removed and the nanomatrixes washed five times with normal saline to remove all soluble proteins. Nanomatrixes were then added to (alkaline phosphatase negative) mammalian cells in culture. It was observed under the microscope that within five minutes, nanomatrixes prepared in the presence of hemagglutinin attach to the cell surfaces and cannot be rinsed away. In contrast, control nanomatrixes synthesized in the absence of hemagglutinin did not attach to cells and were readily removed by rinsing the cells. This means that the hemagglutinin molecules were situated on the surface of the nanomatrixes.

Cells with attached nanomatrixes were then fixed with a standard fixative and stained with a solution containing compounds that would form a dark purple insoluble stain on reaction with alkaline phosphatase. All the nanomatrixes showed uniform dark color after the reaction, indicating that the alkaline phosphatase was incorporated uniformly and evenly distributed within the interior or matrix of the nanomatrixes.

CONCLUSION

The biologically active molecules can be incorporated uniformly and evenly distributed within the interior or matrix of the nanomatrixes, if added before the addition of the alcohol.

Alternatively, the biologically active molecules can be incorporated uniformly on the surfaces of the nanomatrixes, if added immediately after the addition of the desolubilizing agent.

EXPERIMENT SEVENTEEN

TITLE Content of nanomatrixes Synthesized under conditions and the number of particles per ml

EXPERIMENT

Referring to Table 18, the experimental conditions of Tube 77 and Tube 87 were repeated, except that instead of 1 mi, all components were scaled up 1000 fold to 1 liter volume. It was found that many different ways of separating the nanomatrixes from the synthesis media are effective, including a combination of methods selected from the group consisting of dialysis, centrifugation, ultrafiltration, electrodialysis, absorption to solid surface and chromatography.

It was decided that the simplest method is sedimentation by gravity. After 3 washings with normal saline, the nanomatrixes were again allowed to settle by gravity and the supernatant layer removed by suction. The very dense suspension of nanomatrixes were analyzed as to the number of particles per ml (by examination under hemocytometer after proper dilution) and by standard biochemical analysis as to the amount of Hb and HSA as percentages of total nanomatrix proteins.

CONCLUSION

The nanomatrixes have Hb contents comparable to that in patient blood.

TABLE 18

COMPARISON OF NONOMATRIXES WITH ERYTHROCYTES

| | Erythrocytes | Nano-matrixes-87 | Nano-matrixes-77 |
|---|---|---|---|
| RBC Count (billion/ml) | 3.5-5.9 | 1.1 | 9.0 |
| Mean Diameter (micron) | 7 | 2.5 | 1.7 |
| Hb as % of total protein in sphere | | 87.5% | 96.1% |
| HSA as % of total protein in sphere | | 12.5% | 3.9% |
| Hb concentration in fluid (mg/dl) | 12-16 | 5.9 | 12.8 |
| Total protein (Hb + HSA) concentration (mg/ml) | | 6.7 | 13.3 |

EXPERIMENT EIGHTEEN

TITLE Effect of hematin on the formation of nanomatrixes

EXPERIMENT

The reason for adding hematin to the HSA before interaction with Hb was as follows: HSA has many sites for binding the heme derived from Hb. Methemoglobin is known to lose the heme group easily. If the formation of spherical stable monodispersed nanomatrixes depends on the formation of . . . HSA-heme-HSA-heme-HSA . . . non-covalent bonds (cross-linkage or cross-affinity), then saturation of all the heme-binding sites on the HSA molecule by hematin will prevent formation of nanomatrixes.

HSA solutions were incubated with various amounts of bovine hematin purchased from Sigma Chemical Company to result in the concentration of HSA being 25 mg/ml and that of hematin being 12.5, 10.0, 7.5, 5.0, 2.5 and 0.0 mg per ml in each of six tubes respectively.

An aliquot of 0.05 ml was taken from each of these six tubes and added to a second set of six tubes containing 5 mg Hb per 0.95 ml normal saline. Subsequently, 0.10 ml of n-Butanol was added to the mixture and the tubes well shaken to produce turbidity. Immediately after turbidity was seen, each tube was added another 0.05 ml of HSA which had been preincubated with the respective concentration of hematin to make sure that there is no post-synthesis aggregation of nanomatrixes due to insufficient amount of HSA.

CONCLUSION

All six tubes had nanomatrix formation which were monodispersed, stable to aggregation and stable to washing in hypotonic 0.009% saline. This means that presaturation of heme-binding sites on the HSA does not prevent formation of nanomatrixes.

EXPERIMENT NINETEEN

TITLE Synthesis of DNA-containing nanomatrixes

EXPERIMENT

Tube One contains 0.4 ml of a human serum albumin (250 mg/ml) mixed with 0.1 ml of a stroma free human hemoglobin solution (60 mg/ml, containing more than 10% as methemoglobin). To tube one was added 0.5 ml of a DNA solution (1.0 microgram dissolved in normal saline) with shaking to mix well. Ethyl alcohol (200 proof) was added dropwisely (approximately 0.4 ml) until turbidity appears. After the formation of nanomatrixes (examined to be 0.2 microns subsequently by microscopy), the entire suspension was divided equally into two tubes (tube 2, and tube 3). Tube 2 received 0.1 ml of a glutaraldehyde solution (0.01% v/v in normal saline), while tube 3 received 0.1 ml of normal saline as control solution. After another 5 minutes, both tube 2 and tube 3 received 3 ml of normal saline to dilute the nanomatrix suspension.

Assay of the DNA content in tube 2 and tube 3 both showed that more than 90% of the DNA were entrapped inside and on the surface of the nanomatrixes. After removal of the DNA in the supernatant, both DNA containing nanomatrixes were incubated in DNA-free media overnight. No DNA was found to leak out of the nanomatrixes. Attempts to degrade entrapped DNA released less than 5% of all the nanomatrix-bound DNA, suggesting that most of them were contained in the interior of the nanomatrixes. The similarity between the nanomatrixes in tube 2 and tube 3 suggested that addition of the cross-linking agent is purely optional and does not contribute to the formation of the nanomatrix itself.

CONCLUSION

DNA can be successfully entrapped inside the nanomatrixes produced by the method of the present invention, and the use of cross-linking agent is purely optional for the present invention method.

EXPERIMENT TWENTY

TITLE Attachment of DNA and RNA to the surface of preformed nanomatrixes

EXPERIMENT

Control nanomatrixes were synthesized in accordance with Experiment 19 tube 2 and tube 3 conditions except that no RNA was added (0.5 ml of normal saline was added to tube one). Ethanol was removed by dialysis overnight in 1000× excess of normal saline.

Subsequently, approximately 0.02 microgram of RNA was mixed with microliter of the preformed control nanomatrix suspensions, after which the nanomatrixes were separated from the supernatant by high speed centrifugation. Analysis of the RNA content indicated about 50% of the RNA became attached to the surface of the preformed nanomatrixes.

Control nanomatrixes were again synthesized in accordance with Experiment 19 tube 2 and tube 3 conditions except that no DNA was added (0.5 ml of normal saline was added to tube one). Ethanol was removed by dialysis overnight in 100× excess of normal saline.

Subsequently, approximately 0.1 microgram of DNA was mixed with 100 microliter of the preformed control nanomatrix suspensions, after which the nanomatrixes were separated from the supernatant by high speed centrifugation. Analysis of the DNA content of the nanomatrixes indicated at least 90% of the DNA became attached to the preformed nanomatrixes.

CONCLUSION

Both DNA and RNA can successfully attach to the surfaces of the nanomatrixes produced by the method of the present invention.

EXPERIMENT TWENTY-ONE

TITLE DNA molecules are protected by incorporation in the interior or by attachment on the surface of nanomatrixes from the degradation by endonuclease

EXPERIMENT

Nanomatrixes with DNA incorporated inside (DNA-in-spheres) or with DNA attached on the outside (DNA-outspheres) were synthesized as follows:

1. DNA-in-Spheres

Five microliters of hemoglobin solution (60 mg/ml) is mixed with 20 microliters of human serum albumin (250 mg/ml) and 20 microliters of DNA solution (containing 12.5 microgram of DNA). 18 microliters of ethanol was quickly added to result in 63 microliters of suspension containing nanomatrixes. Analysis of the DNA content in the supernatant and inside the nanomatrixes showed that 90% of all added DNA is associated with the nanomatrixes.

The yield of nanomatrixes was approximately 20%. This means that at least 11.25 micrograms of DNA can be captured by 1.06 mg of nanomatrixes. The upper limits of DNA capable of being captured per nanomatrixes is not known yet. It is believed that one milligram of nanomatrixes can bind up to one milligram of DNA.

2. DNA-out-spheres

Five microliters of hemoglobin solution (60 mg/ml) is mixed with 20 microliter of human serum albumin (250 mg/ml). Ten microliters of ethanol was quickly added to result in 35 microliters of suspension containing nanomatrixes. 20 microliters of DNA solution (containing 12.5 microgram of DNA) was then added to the nanomatrix suspension. Analysis of the DNA content in the supernatant and DNA associated with the nanomatrixes showed that again 90% of all added DNA is associated with the nanomatrixes.

The yield of nanomatrixes was also approximately 20%. This means that at least 11.25 micrograms of DNA can be captured by 1.06 mg of nanomatrixes. The upper limits of DNA per nanomatrixes obtained by this method has not been obtained yet. It is believed that one milligram of nanomatrixes can bind up to one milligram of DNA.

3. Protection from the degradation by endonuclease

To show protection from the degradation by endonuclease, aliquots of DNA in-spheres and DNA out-spheres (approximately 10 microliters each) were incubated with an endonuclease preparation for 30 minutes at 37 degrees centigrade. Subsequently, the suspensions were centrifuged to separate the supernatant from the nanomatrixes (which formed pellets in the centrifuge tubes). Migration patterns of the DNA bands (from DNA in the supernatant) in gel electrophoresis are consistent with DNA pieces degraded at the predicted endonuclease sites.

The pellets were treated as follows: 50 microliters of EDTA (ethylenediaminetetraacetic acid) solution (50 millimolar) were layered onto the pellets carefully without disturbing the pellets. The presence of EDTA, a chelating agent, stops the activity of any endonuclease left over so that any DNA subsequently released from their association with the nanomatrixes will not be degraded after the nanomatrixes were solubilized. Five microliters of a weak alkaline solution (0.003 normal NAOH) were added to each of the DNA-in-sphere pellet and the DNA-out-sphere pellet.

After incubation for 10 minutes at 37 degrees centigrade, five microliters of SDS (10 mg/ml) solution were added and the previous turbid suspensions became clear, indicating that the protein molecules constituting the nanomatrixes came apart again and the nanomatrixes were completely solubilized. Migration patterns of the released DNA (from both DNA-in-spheres and DNA-out-spheres) in gel electrophoresis were identical to control naked DNA molecules which were not degraded.

CONCLUSION

Whether DNA is hidden in the interior of the nanomatrixes or attached on the surface of the nanomatrixes, they became protected from enzymatic degradation. Large amounts of DNA can be protected by these methods. The mechanisms of protection is not known. It is possible that DNA vulnerable sites were covered by the protein molecules so that the endonuclease cannot reach them, or the stereohinderance presented by the DNA's association with the nanomatrixes prevents the proper orientation of the endonuclease or the DNA molecules. Alternatively, co-factors needed by the degradative process may not be available on the surface or interior of nanomatrixes for the enzymatic action to proceed. DNA incorporated in the interior or attached on the surface of the nanomatrixes were not damaged in any way and could be released again in intact form from these nanomatrixes.

DEFINITION OF THE PRESENT INVENTION

The present invention is defined as a method of producing monodispersed and stabilized porous and membraneless nanomatrixes for carrying medication for in vivo administration, where the nanomatrixes are typically larger than 1 micron but less than 4 microns in diameter, and stable against aggregation and re-solubilization in hypotonic saline for at least 24 hours.

Defined in detail, the present invention is a method of producing nanomatrixes for carrying medication for in vivo administration, comprising the steps of: (a) dissolving a first type of protein in a buffer of suitable osmolarity of approximately 280±80 milliosmos, where the first type of protein is hemoglobin; (b) adding a second type of protein into said buffer containing said first type of protein, such that the weight ratio of said first and second type of proteins is approximately 2:1, where the second type of protein is albumin protein; (c) adding a solution containing an organic solvent into said buffer containing said first and second type of proteins, such that the organic solvent is approximately 0.14±0.06 volume by one volume of said buffer containing said first and second type of proteins, where said organic solvent is an alcohol selected from the group consisting of methanol, ethanol, propanol and butanol; and (d) mixing said buffer containing said first and second type of proteins and said solution containing said organic solvent, resulting in a stabilized turbid suspension containing monodispersed and stabilized nanomatrixes which are typically larger than 1 micron but less than 4 microns in diameter, and stable against aggregation and re-solubilization in hypotonic 0.009% saline for at least 24 hours.

Defined broadly, the present invention is a method of producing nanomatrixes for carrying medication for in vivo administration, comprising the steps of (a) dissolving a first type of protein in a buffer of suitable osmolarity of approximately 280±80 milliosmos, where the first type of protein is hemoglobin; (b) adding a first solution containing an organic solvent into said buffer containing said first type of protein, such that the organic solvent is approximately 0.14±0.06 volume by one volume of said buffer containing said first type of protein, where said organic solvent is an alcohol selected from the group consisting of methanol, ethanol, propanol and butanol; (c) mixing said buffer containing said first type of protein and said first solution containing said organic solvent, resulting in a turbid suspension containing monodispersed nanomatrixes which are stable against re-solubilization; (d) adding a second solution containing a second type of protein into said turbid suspension containing said monodispersed nanomatrixes, such that the weight ratio of said first and second type of proteins is approximately 2:1, where the second type of protein is albumin protein; and (e) mixing said second solution containing said second type of protein and said turbid suspension containing said monodispersed nanomatrixes, resulting in a stabilized turbid suspension containing monodispersed and stabilized nanomatrixes which are typically larger than 1 micron but less than 4 microns in diameter, and stable against aggregation and re-solubilization in hypotonic 0.009% saline for at least 24 hours.

Defined more broadly, the present invention is a method of producing nanomatrixes for carrying medication for in vivo administration, comprising the steps of: (a) dissolving a first type of protein in a buffer of suitable osmolarity of approximately 280±80 milliosmos, where the first type of protein is hemoglobin; (b) adding a second type of protein into said buffer containing said first type of protein, such that the weight ratio of said first and second type of proteins is approximately 4:1, where the second type of protein is albumin protein; (c) adding a first solution containing an organic solvent into said buffer containing said first and second type of proteins, such that the organic solvent is approximately 0.14±0.06 volume by one volume of said buffer containing said first and second type of proteins, where said organic solvent is an alcohol selected from the group consisting of methanol, ethanol, propanol and butanol;

(d) mixing said buffer containing said first and second type of proteins and said first solution containing said organic solvent, resulting in a turbid suspension containing monodispersed nanomatrixes which are stable against re-solubilization; (e) adding a second solution containing a third type of protein into said turbid suspension containing said monodispersed nanomatrixes, such that the weight ratio of said first and third type of proteins is approximately 4:1, where the third type of protein is selected from the group consisting of albumin, immunoglobulin and ligand; and (f) mixing said second solution containing said third type of protein and said turbid suspension containing said monodispersed nanomatrixes, resulting in a stabilized turbid suspension containing monodispersed and stabilized nanomatrixes which are typically larger than 1 micron but less than 4 microns in diameter, and stable against aggregation and re-solubilization in hypotonic 0.009% saline for at least 24 hours.

The present invention is defined alternatively as a device of monodispersed and stabilized porous and membraneless nanomatrixes for carrying medication for in vivo administration, where the nanomatrixes are typically larger than 1 micron but less than 4 microns in diameter, and stable against aggregation and re-solubilization in hypotonic saline for a sufficient period of time.

Defined alternatively, the present invention is a device of stable porous and membraneless nanomatrixes for carrying medication for in vivo administration, where the nanomatrixes are typically larger than 1 micron but less than 4 microns in diameter, and stable against aggregation and resolubilization in hypotonic 0.009% saline for at least 24 hours, the device having a composition of a first type of protein which is hemoglobin, a second type of protein which is albumin, and a biologically active substance which is entrapped within the nanomatrixes, where the weight ratio of the first type of protein, the second type of protein and the biologically active substance is within the range of approximately 87:13:10 and 97:3:10.

Defined also alternatively, the present invention is a device of stable porous and membraneless nanomatrixes for carrying medication for in vivo administration, where the nanomatrixes are typically larger than 1 micron but less than 4 microns in diameter, and stable against aggregation and re-solubilization in hypotonic 0.009% saline for at least 24 hours, the device having a composition of a first type of protein which is hemoglobin, a second type of protein which is albumin, and a biologically active substance which is bound on the surfaces of the nanomatrixes, where the weight ratio of the first type of protein, the second type of protein and the biologically active substance is within the range of approximately 87:13:10 and 97:3:10.

Defined alternatively and broadly, the present invention is a device of stable porous and membraneless nanomatrixes for carrying medication for in vivo administration, where the nanomatrixes are typically larger than 1 micron but less than 4 microns in diameter, and stable against aggregation and re-solubilization in hypotonic 0.009% saline for at least 24 hours, the device having a composition of a first type of protein which is hemoglobin, a second type of protein which is albumin, and a biologically active substance which is carried by the nanomatrixes, where the weight ratio of the first type of protein, the second type of protein and the biologically active substance is within the range of approximately 87:13:10 and 97:3:10.

Defined alternatively and more broadly, the present invention is a device of stable porous and membraneless nanomatrixes for carrying medication for in vivo administration, where the nanomatrixes are typically larger than 1 micron but less than 4 microns in diameter, and stable against aggregation and re-solubilization in hypotonic 0.009% saline for at least 24 hours, the device having a composition of a first type of protein which is hemoglobin and a second type of protein which is albumin, where the weight ratio of the first and second type of proteins is within the range of approximately 87:13 and 97:3.

Of course the present invention is not intended to be restricted to any particular form or arrangement, or any specific embodiment disclosed herein, or any specific use, since the same may be modified in various particulars or relations without departing from the spirit or scope of the claimed invention hereinabove shown and described of which the apparatus shown is intended only for illustration and for disclosure of an operative embodiment and not to show all of the various forms or modification in which the present invention might be embodied or operated.

The present invention has been described in considerable detail in order to comply with the patent laws by providing full public disclosure of at least one of its forms. However, such detailed description is not intended in any way to limit the broad features or principles of the present invention, or the scope of patent monopoly to be granted.

What is claimed is:

1. A composition comprising stable porous and membraneless nanomatrixes for carrying medication for in vivo administration, where the nanomatrixes are typically larger than 1 micron but less than 4 microns in diameter, and stable against aggregation and re-solubilization in hypotonic 0.009% saline for at least 24 hours, the nanomatrixes consisting of hemoglobin and albumin, where the weight ratio of said hemoglobin and albumin is between approximately 57:43 and 92:8.

2. The invention as defined in claim 1 wherein said hemoglobin is human hemoglobin and said albumin is human serum albumin.

3. The invention as defined in claim 1 wherein said hemoglobin is a naturally occurring hemoglobin.

4. The invention as defined in claim 1 wherein said hemoglobin is polymerized hemoglobin.

5. The invention as defined in claim 1 wherein said hemoglobin is pyridoxylated-hemoglobin.

* * * * *